(12) United States Patent
Clossen-von Lanken Schulz et al.

(10) Patent No.: US 7,779,695 B2
(45) Date of Patent: Aug. 24, 2010

(54) METHOD AND DEVICE FOR DETERMINING DEFECTS ON A CONSTRUCTIONAL ELEMENT OF A TURBINE

(75) Inventors: Michael Clossen-von Lanken Schulz, Geldern (DE); Michael Opheys, Nettetal (DE)

(73) Assignee: Siemens Aktiengesellschaft, Munich (DE)

( * ) Notice: Subject to any disclaimer, the term of this patent is extended or adjusted under 35 U.S.C. 154(b) by 146 days.

(21) Appl. No.: 11/795,942

(22) PCT Filed: Dec. 30, 2005

(86) PCT No.: PCT/EP2005/057229
§ 371 (c)(1),
(2), (4) Date: Jul. 24, 2007

(87) PCT Pub. No.: WO2006/079443
PCT Pub. Date: Aug. 3, 2006

(65) Prior Publication Data
US 2008/0134791 A1 Jun. 12, 2008

(30) Foreign Application Priority Data
Jan. 27, 2005 (DE) .................. 10 2005 003 959
Feb. 4, 2005 (EP) .................. 05002363

(51) Int. Cl.
*G01N 29/24* (2006.01)
(52) U.S. Cl. .................. 73/625; 73/622; 73/628; 73/865.8
(58) Field of Classification Search .................. 73/625, 73/618, 620, 622, 626, 602, 583, 596, 600, 73/865.8
See application file for complete search history.

(56) References Cited

U.S. PATENT DOCUMENTS

| 4,242,912 | A | | 1/1981 | Burckhardt et al. |
|---|---|---|---|---|
| 6,034,760 | A | * | 3/2000 | Rees ..................... 356/28.5 |
| 6,082,198 | A | | 7/2000 | Sabourin et al. |
| 6,089,096 | A | | 7/2000 | Alexandru |
| 7,010,982 | B2 | * | 3/2006 | Bergman ..................... 73/618 |
| 7,293,461 | B1 | * | 11/2007 | Girndt ..................... 73/622 |
| 2003/0136195 | A1 | | 7/2003 | Krieg et al. |
| 2004/0020296 | A1 | | 2/2004 | Moles et al. |
| 2008/0245151 | A1 | * | 10/2008 | Roney et al. ..................... 73/628 |
| 2009/0078742 | A1 | * | 3/2009 | Pasquali et al. ..................... 228/103 |

FOREIGN PATENT DOCUMENTS

| CN | 1412551 A | | 4/2003 |
|---|---|---|---|
| EP | 1 484 608 A2 | | 12/2004 |
| EP | 1 491 914 A2 | | 12/2004 |
| JP | 360107562 A | * | 6/1985 |
| JP | 411174030 | * | 7/1995 |
| JP | 2007163470 A | * | 6/2007 |

\* cited by examiner

*Primary Examiner*—J M Saint Surin

(57) ABSTRACT

The invention relates to a method which is used to detect defects on a component of a turbine. Said method comprises the following steps; at least one ultrasonic signal is emitted and captured by means of a group beam examination head on a flat region of the component which is to be examined. The invention is characterized according to the following steps: the group of the beam examination heads are distributed into several virtual examination heads and at least one ultrasonic signal is emitted and captured by at least two of the virtual examination heads which is directed to an individual flat region which is to be examined.

5 Claims, 4 Drawing Sheets

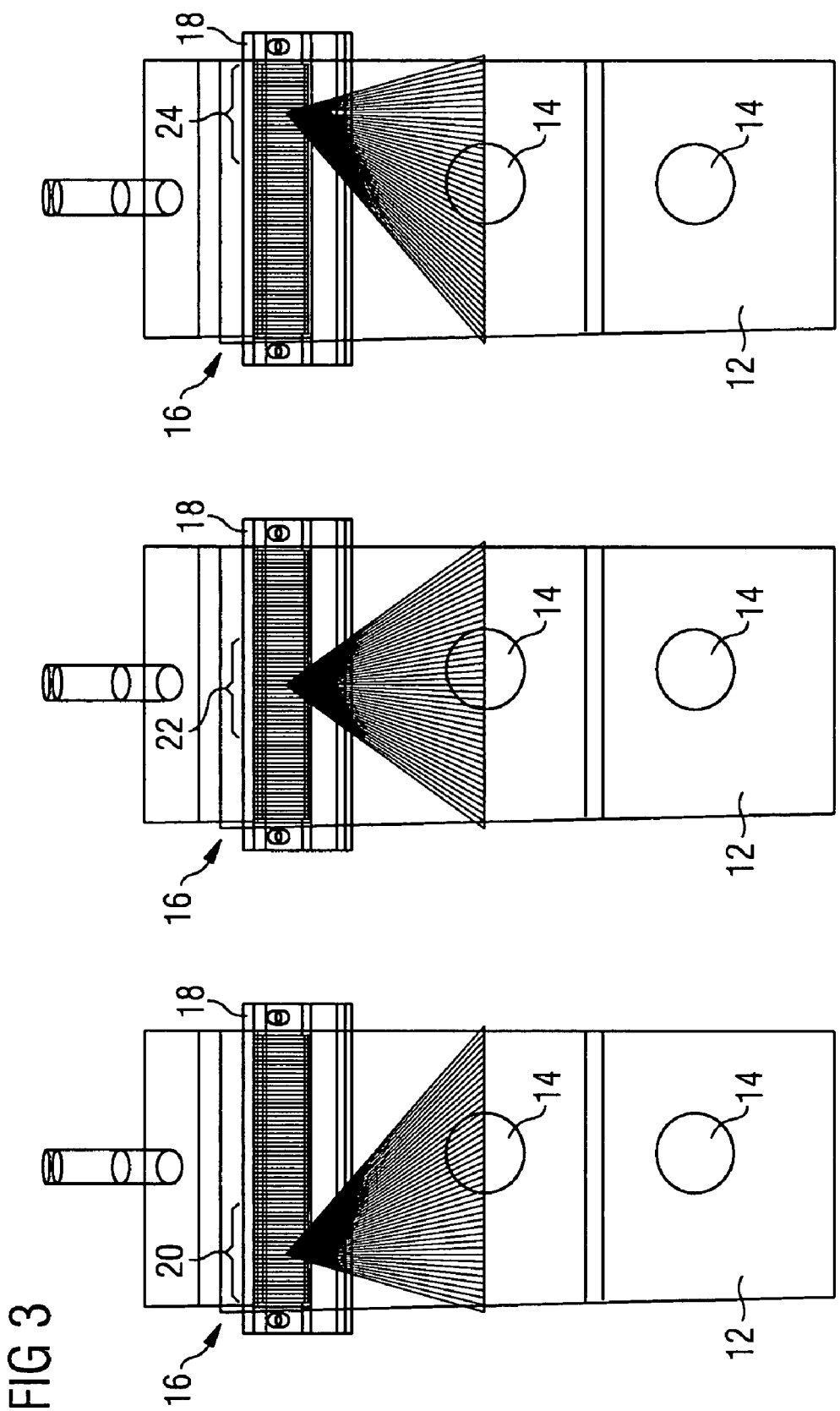

METHOD AND DEVICE FOR DETERMINING DEFECTS ON A CONSTRUCTIONAL ELEMENT OF A TURBINE

CROSS REFERENCE TO RELATED APPLICATIONS

This application is the US National Stage of International Application No. PCT/EP2005/057229, filed Dec. 30, 2005 and claims the benefit thereof. The International Application claims the benefits of German application No 10 2005 003 959.6 filed on Jan. 27, 2005 and European application No. 05002363.9 filed Feb. 4, 2005, all of the applications are incorporated by reference herein in their entirety.

FIELD OF INVENTION

The invention relates to a method for determining defects on a constructional element of a turbine, with the steps of sending and receiving of at least one ultrasonic signal by means of a phased array probe on a surface region, which is to be inspected, of the constructional element. In addition, the invention relates to a measuring and evaluating device for determining defects on a constructional element of a turbine, with a phased array probe for transmitting and receiving at least one ultrasonic signal on a surface region, which is to be inspected, of the constructional element.

BACKGROUND OF INVENTION

For determining defects on a constructional element of a turbine, like, for example, a turbine blade, it is basically known to carry out an ultrasonic inspection. Such inspections, on account of the geometries which exist in the case of such constructional elements, however, are only possible to a very limited extent and are also comparatively error-prone.

So, for example, at the present time a corresponding inspection of fastening holes of finger pin roots on turbine blades is possible only after removal of the blades.

SUMMARY OF INVENTION

By the use of the phased array technique, a fault on the surface region, which is to be inspected, can be indicated by means of an imaging display without manipulation of the probe. This already represents an improvement, since it can especially dispense with a time-intensive and therefore costly removal and installation of turbine blades. By means of the phased array technique, in particular the direction of the radiated ultrasound, or the direction from which the ultrasound can be received, as the case may be, can be altered.

By means of the phased array technique, for example, it is possible to carry out safe and quick analyses in an anticipated fault region of turbine blade roots. In doing so, especially cracks can be detected, which, as a result of high mechanical, thermal or corrosive stress, emerge as fatigue cracks or vibration cracks.

According to the invention, this phased array technique is now improved to the effect that the phased array probe is divided into a plurality of virtual probes, and then at least one ultrasonic signal by at least two of the virtual probes is transmitted in a directed manner onto an individual surface region which is to be inspected. The echo signals from the surface region which is to be inspected are received by the at least two virtual probes which are provided according to the invention. In this case, the impulse echo method is advantageously applied, since by this technique defects can be basically especially accurately determined.

The measuring and evaluating device according to the invention is provided with a phased array probe for this purpose, which is divided into a plurality of virtual probes, and a control unit is provided, by which by at least two of the virtual probes at least one ultrasonic signal in each case can be transmitted in a directed manner onto the individual surface region which is to be inspected, and received.

By transmitting and receiving ultrasonic signals by a plurality of virtual probes, the surface region which is to be inspected is observed, so to speak, from a plurality of viewing directions. The result of the inspection is correspondingly also more accurate and less error-prone.

The phased array probe according to the invention is especially advantageously divided into three virtual probes with especially about 24 elements in each case. For this purpose, for example, in all 64 elements can be originated from one probe and are then circuit-technologically divided into three probes which are to be separately controlled.

Each of the virtual probes, for example, is advantageously controlled by programming of the associated ultrasonic device so that a plurality of shots can be emitted onto the surface region which is to be monitored. For example, 200 such shots are preferably emitted from each of the virtual probes, and their echo signals received accordingly. The emitting of the shots in this case is advantageously carried out in such a way that the shots or the emitted ultrasonic signals, as the case may be, traverse or oscillate over the surface region which is to be inspected. For this purpose, the phased array probe can preferably be formed as a linear oscillator with an as high as possible number of elements and/or with an exchangeable wedge.

The position and/or the form of possible defects on the constructional element according to the invention can advantageously follow by combination of the measurement results of the at least two virtual probes on the individual surface region which is to be inspected, or by means of a comparison with a reference measurement result. Especially the surface extent or the magnitude of the fault can be especially accurately determined in the process, because as a rule at least one of the inspection traversing movements has clearly recorded the contour of the fault which is to be determined.

In addition, especially the orientation of a defect on the constructional element by means of a comparison of the measurement results of the at least two virtual probes on the individual surface region which is to be inspected, or relative to a reference measurement result, can be determined by the course of action according to the invention. Such an assessment and identification especially of the orientation of cracks on the constructional element which is to be inspected is based on the fact that as a rule one of the traversing movements according to the invention irradiates into the crack, while other traversing movements, if applicable, basically traverse over the crack transversely to its orientation.

For an assessment of the inspection results which are determined according to the invention, which is as realistic as possible and especially easy to be carried out by corresponding evaluating devices or evaluating personnel, it is especially advantageous if the measuring and evaluating device according to the invention is adapted for producing in an imaging process a two-dimensional display of the measurement results of the at least two virtual probes. In this case, the amplitude level of the echo signal is especially preferably indicated in a color-coded manner. This can especially be carried out in a B-scan, by which a two-dimensional display of the measurement results is possible.

BRIEF DESCRIPTION OF THE DRAWINGS

An exemplary embodiment of a method according to the invention for determining defects on a constructional element of a turbine, and of a measuring and evaluating device according to the invention for determining such defects, is explained in detail in the following, with reference to the attached schematic drawings. In the drawing:

FIG. 3 shows three sketches for explaining the construction of a measuring and evaluating device according to the invention.

DETAILED DESCRIPTION OF INVENTION

Figure 2:
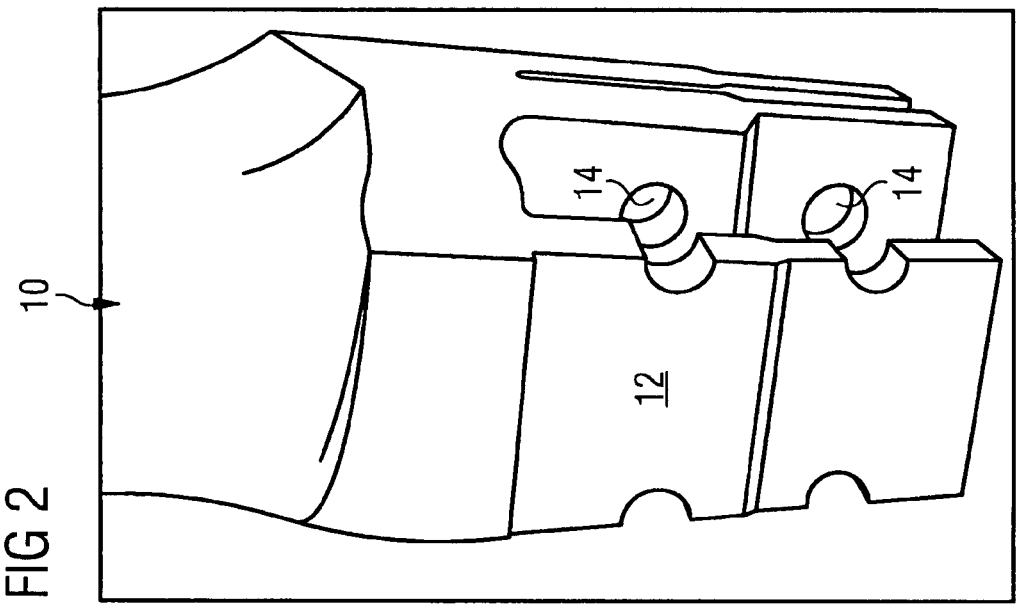
FIG. 2 shows a second perspective view of the component according to FIG. 1.
Figure 1:
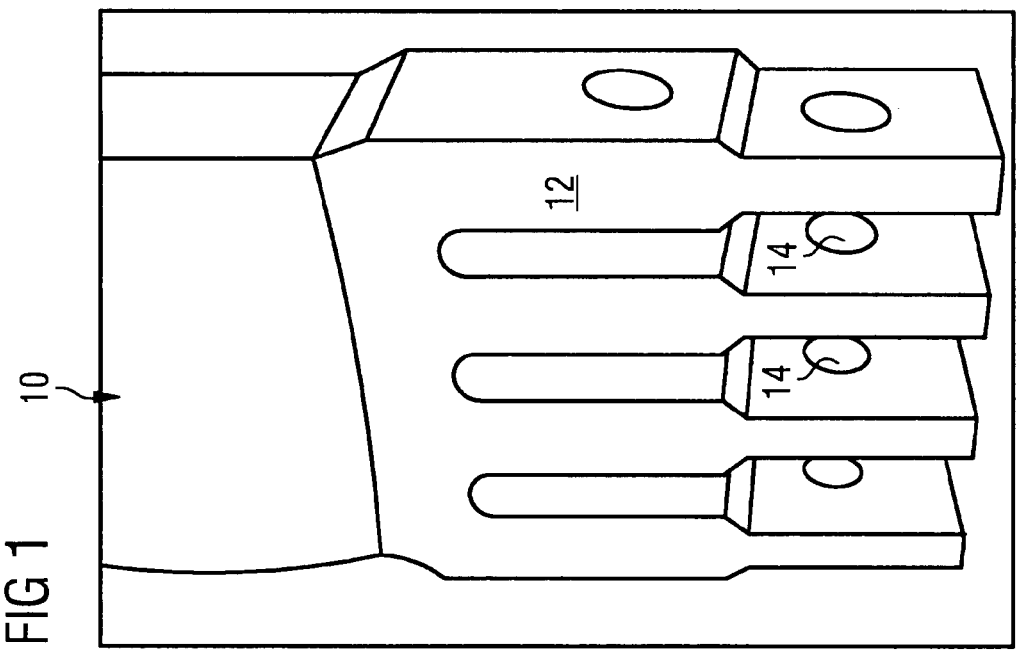
FIG. 1 shows a first perspective view of an inspected component according to the invention.

In FIG. 1, a turbine blade 10 is shown, which is provided for attaching on a turbine shaft or a wheel disk, which is not shown, of a turbine. Such a turbine blade 10, during operation of the turbine, is subjected to a high thermal and also mechanical stress.

The turbine blade 10 has a blade root 12, which is designed as a finger pin root, with disc-shaped webs through which fastening holes 14 are formed. As a result of the aforementioned stresses, a crack formation can especially occur at the fastening holes 14.

A safe inspection of such damage of the turbine blades 10 at the present time is only possible in the removed state of the turbine blades 10. An inspection in the installed state by means of an ultrasound technique is possible only to a limited degree, and is comparatively error-prone.

Figure 5:
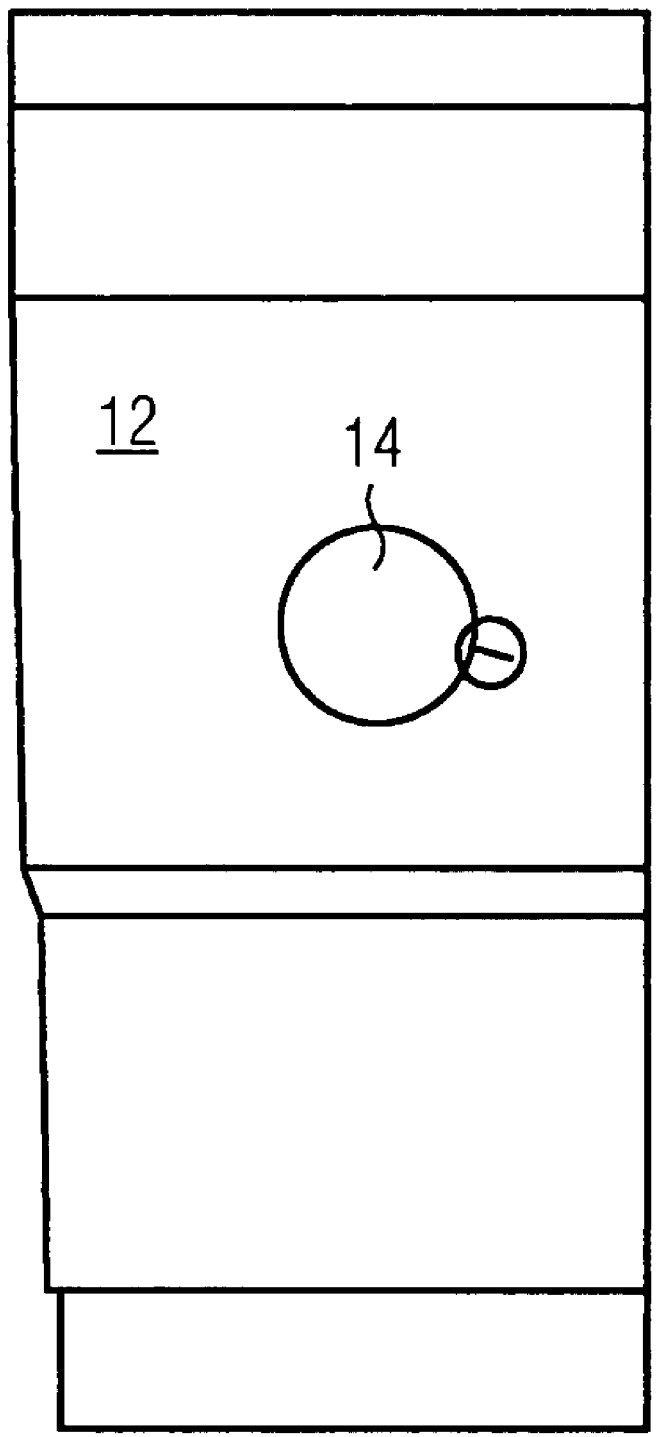
FIG. 5 shows the surface region on a component which in this case is inspected, according to FIGS. 1 and 2.

In order to improve the inspection, a phased array probe is used in a phased array technique, and this probe is arranged in a stationary manner on the turbine blade 10 and/or on the associated shaft. The arrangement is effected in such a way that the surface region which is to be inspected, as it is illustrated, for example, by a circle in FIG. 5, can be irradiated. A manipulation of the probe in this case is not necessary.

The measuring and evaluating device 16 used in this case, which is roughly shown in FIG. 3, is adapted in such a way that its phased array probe 18 is divided into three virtual probes 20, 22 and 24.

Of these virtual probes 20, 22 and 24, a first comprises elements 1 to 24 of the phased array probe 18 which altogether comprises 64 elements. In a corresponding way, the second virtual probe 22 comprises elements 21 to

44 of the phased array probe, and the third virtual probe 24 comprises elements 41 to 64 of the phased array probe.

The individual virtual probes 20, 22 and 24 are controlled by a control unit, which is not shown in detail, in such a way that individual shots, about 200 in the present example, are transmitted by them in each case as a traversing movement by means of a linear oscillator over the surface region which is to be inspected, and the echo signals are subsequently received.

The echo signals of all shots of a virtual probe are then displayed in a B-scan and provide an imaging process with a two-dimensional display. In the display, the echo signals are shown in a color-coded manner with regard to their amplitude level. This indication is reproduced by the B-scan graphics, with correspondingly associated A-scan graphics, which are portrayed in FIG. 4. A separate B-scan graphic is displayed for each virtual probe.

By means of the different virtual probes, the anticipated fault region (as it is exemplarily marked with a circle in FIG. 5) is consequently scanned by sound waves from different viewing angles. This scanning by sound waves from different angles allows the orientation of a fault or defect to be determined.

Figure 4:
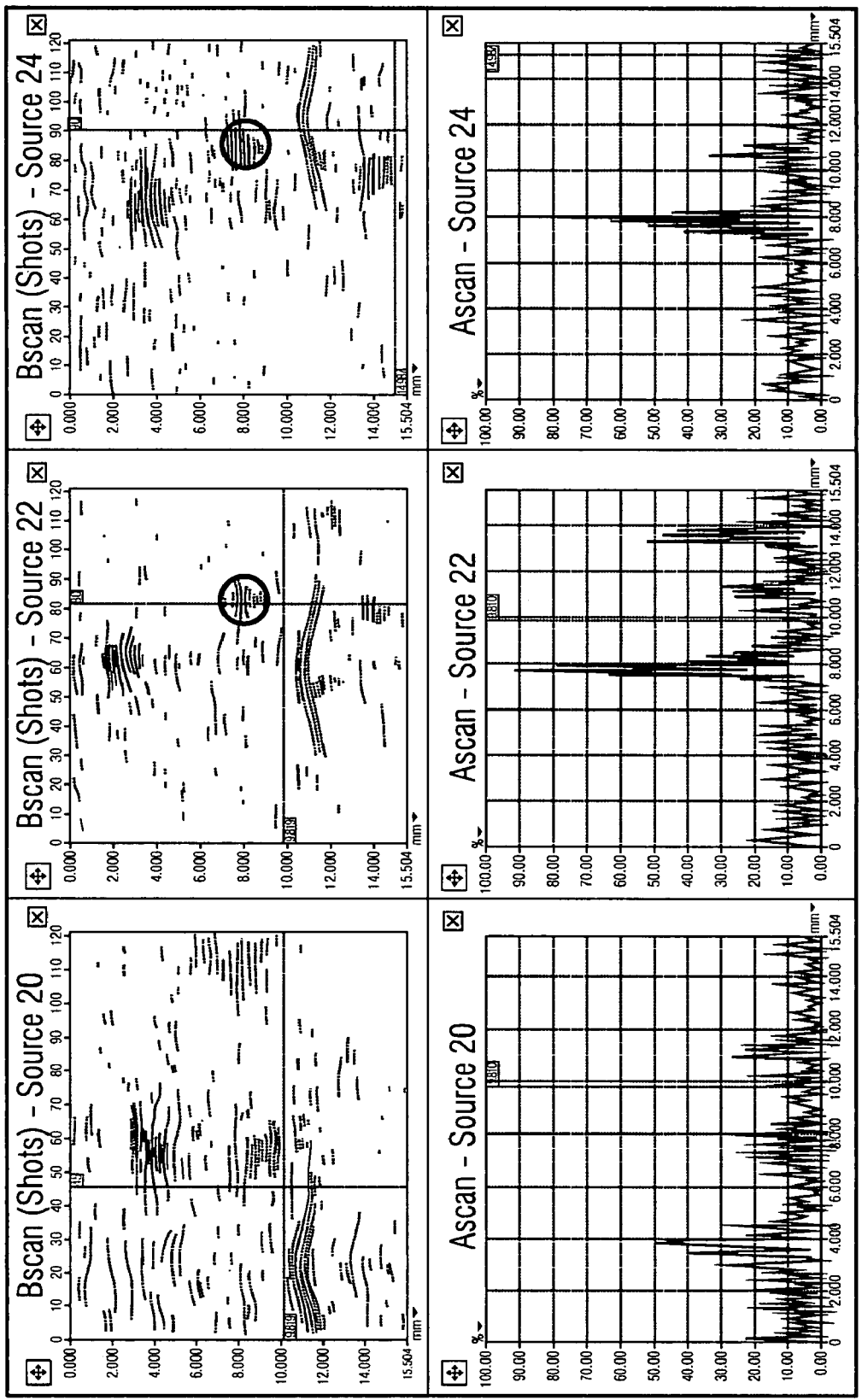
FIG. 4 shows a graphic display of the measurement results of an inspection with the measuring and evaluating device according to FIG. 3

So, for example, it is to be seen on the three B-scan graphics of FIG. 4 that the crack defect, which is marked there by a circle, is clearly identified especially in the inspection by the second and the third virtual probe 22 or 24, as the case may be, whereas it is left undetected by the first virtual probe. This allows a correspondingly better conclusion of the magnitude, precise shape and especially also the direction of the crack defect.

In this way, a quick and reliable inspection with an improved determining of the fault magnitude, fault position and fault orientation, especially of the aforementioned constructional element, becomes altogether possible.

Furthermore, the method according to the invention, and the associated measuring and evaluating device, can also be profitably used with many other types of components in which problems still occur in the case of conventional ultrasonic inspections with phased array probes.

The invention claimed is:

1. A method for determining defects on a constructional element of a turbine using a phased array technique, comprising:

dividing a phased array probe into a plurality of virtual probes that are arranged directly one behind the other in linear fashion forming a linear oscillator;

transmitting an ultrasonic signal via by at least two of the virtual probes in a directed manner over a fixed radial projection to cover a predetermined area on an individual surface region of the constructional element to be inspected wherein each virtual probe produces a plurality of ultrasonic pulses on the individual surface region to be inspected;

receiving the transmitted ultrasonic signal via the phased array probe;

wherein the phased array probe is in a fixed position relative to a fixed position of the construction element during the transmitting and receiving of ultrasonic signals;

evaluating the position and/or the form of possible defects on the constructional element by combination of the measurement results of the plurality of virtual probes on the predetermined individual surface region to be inspected; and, determining the orientation of a defect on the constructional element by comparison of the measurement results of the plurality of virtual probes on the predetermined individual surface region to be inspected.

2. A measuring and evaluating device for determining defects on a constructional element of a turbine, comprising:

a phased array probe for use in a phased array technique for transmitting and receiving ultrasonic signals on a surface region of the constructional element to be inspected, wherein the phased array probe is divided into a plurality of virtual probes arranged directly one behind the other in linear fashion;

a control unit that controls the phased array probe such that a plurality of the virtual probes each transmit and receive an ultrasonic signal directly onto and from a surface region of a constructional element to be inspected; and, wherein the phased array probe is in a fixed position relative to a fixed position of the construction element during the transmitting and receiving of ultrasonic signals, and the ultrasonic signals are transmitted over a fixed radial projection to cover a predetermined area on the construction element for determining if defects exist in that area; and wherein the control unit directs a plurality of ultrasonic signals onto the individual surface region which is to be inspected, evaluates the position and/or the form of possible defects on the constructional element by a combination of the measurement results of the plurality of virtual probes on the individual surface region to be inspected and determines the orientation of a defect on the constructional element by a comparison of the measurement results of the plurality of virtual probes on the individual surface region to be inspected.

3. The device as claimed in claim 2, wherein the phased array probe further comprises a linear oscillator.

4. The device as claimed in claim 3, wherein in an imaging process the control unit produces a two-dimensional display of the measurement results of the plurality of virtual probes.

5. The device as claimed in claim 2, wherein the controller determines a surface extent or magnitude of a defect by comparing the ultrasonic signals received by the controller to a reference measurement result associated the constructional element.

* * * * *